(12) United States Patent
Espina Perez et al.

(10) Patent No.: US 11,116,424 B2
(45) Date of Patent: Sep. 14, 2021

(54) DEVICE, SYSTEM AND METHOD FOR FALL DETECTION

(71) Applicant: KONINKLIJKE PHILIPS N.V., Eindhoven (NL)

(72) Inventors: Javier Espina Perez, Eindhoven (NL); Vincent Alexander Rudolf Aarts, Eindhoven (NL); Aki Sakari Harma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 355 days.

(21) Appl. No.: 16/323,045

(22) PCT Filed: Aug. 8, 2017

(86) PCT No.: PCT/EP2017/070067
§ 371 (c)(1),
(2) Date: Feb. 4, 2019

(87) PCT Pub. No.: WO2018/029193
PCT Pub. Date: Feb. 15, 2018

(65) Prior Publication Data
US 2019/0167157 A1    Jun. 6, 2019

(30) Foreign Application Priority Data
Aug. 8, 2016    (EP) .................................... 16183222

(51) Int. Cl.
*A61B 5/11*    (2006.01)
*A61B 5/00*    (2006.01)
(Continued)

(52) U.S. Cl.
CPC ........... *A61B 5/1117* (2013.01); *A61B 5/1128* (2013.01); *A61B 5/681* (2013.01);
(Continued)

(58) Field of Classification Search
CPC ................................................... A61B 5/1117
See application file for complete search history.

(56) References Cited

U.S. PATENT DOCUMENTS 9,060,683 B2    6/2015    Tran
9,204,796 B2    12/2015    Tran
(Continued)

FOREIGN PATENT DOCUMENTS

CN    105125221    12/2015
CN    205094444    3/2016
(Continued)

OTHER PUBLICATIONS

Atallah L et al: "Behaviour profiling with ambient and wearable sensing", Proceedings of the International Workshop on Wearable Andimplantable Body Sensor Networks, Mar. 26, 2007.
(Continued)

*Primary Examiner* — Travis R Hunnings (57) ABSTRACT

The present invention relates to a device, system and method for reliable and fast fall detection. The device comprises a sensor input (11) for obtaining sensor data related to movement of a subject acquired by a body-worn sensor (20, 22, 61) worn by the subject, and a video input (12) for obtaining video data of the subject and/or the subject's environment. An analysis unit (13) analyzes the obtained sensor data to detect one or more signal features indicative of a potential fall of the subject and for analyzing, if one or more such signal features have been detected, the detected one or more signal features and/or related sensor data in combination with related video data to identify similarities between: changes of the related sensor data and/or the signal features over time; and changes of the video data over time. An
(Continued)

output (14, 64, 65, 66) issues a fall detection indication if the level and/or amount of detected similarities exceeds a corresponding threshold.

13 Claims, 3 Drawing Sheets

(51) Int. Cl.
　　　*G08B 21/04*　　　(2006.01)
　　　*G08B 25/01*　　　(2006.01)
(52) U.S. Cl.
　　　CPC .......... *A61B 5/7246* (2013.01); *G08B 21/043* (2013.01); *G08B 21/0446* (2013.01); *G08B 21/0476* (2013.01); *G08B 21/0492* (2013.01); *G08B 25/016* (2013.01); *A61B 5/6803* (2013.01); *A61B 2562/0219* (2013.01)

(56) References Cited

U.S. PATENT DOCUMENTS

| | | | |
|---|---|---|---|
| 2012/0314901 A1* | 12/2012 | Hanson | A61B 5/1117 382/103 |
| 2014/0266787 A1 | 9/2014 | Tran | |
| 2015/0112151 A1* | 4/2015 | Muhsin | A61B 5/0013 600/301 |
| 2015/0318015 A1* | 11/2015 | Bose | A63F 13/212 386/248 |

FOREIGN PATENT DOCUMENTS

| | | |
|---|---|---|
| WO | 2011/016782 | 2/2011 |
| WO | 2013054257 | 4/2013 |

OTHER PUBLICATIONS

Sathyanarayana, et al: "Vision-based patient monitoring: a comprehensive review of algorithms and technologies", Journal of Ambient Intelligence and Humanized Computing, Springer Verlag, First Online: Nov. 26, 2015.

Medrano, et al: "Personalizable Smartphone Application for Detecting Falls", Biomedical and Health Informatics (BHI), 2014 IEEE-EMBS International Conference, IEEE, 2014.

Chan, et al: "Wireless Patch Sensor for Remote Monitoring of Heart Rate, Respiration, Activity, and Falls", 35th Annual International Conference of the IEEE EMBS, IEEE, 2013.

Narasimhan, et al: "Skin-Contact Sensor for Automatic Fall Detection", 34th Annual International Conference of the IEEE EMBS, IEEE, 2012.

* cited by examiner

DEVICE, SYSTEM AND METHOD FOR FALL DETECTION

CROSS REFERENCE TO RELATED APPLICATIONS

This application is the U.S. National Phase application under 35 U.S.C. § 371 of International Application No. PCT/EP2017/070067 filed Aug. 8, 2017 published as WO 2018/029193 on Feb. 15, 2018, which claims the benefit of European Patent Application Number 16183222.5 filed Aug. 8, 2016. These applications are hereby incorporated by reference herein.

FIELD OF THE INVENTION

The present invention relates to a device, system and method for fall detection.

BACKGROUND OF THE INVENTION

Falling is a widely recognized issue that adversely affects the lives of a substantial part of the population, including elderly, hospital patients, and people with assistance requirements. Fall detectors provide a notification/alarm about a person having fallen. This can fulfil the needs of providing earlier assistance, better incident reporting, and may prevent (some) recurrence of falls. A number of fall detectors based on wearable sensors have been described and are commercially available. Fall detectors based on video data are also known, although they have not yet found their way into valid products.

Fall detectors based solely on wearable sensors often exhibit insufficient detection accuracy in demanding situations. Moreover they do not provide the location of the fallen wearer, which can delay proper assessment of the event localization of the wearer and the arrival of assistance. Fall detectors based solely on video data are currently immature, generally exhibiting poor detection accuracy in realistic usage conditions and known issues with occlusions and poor lighting conditions.

US 2015/0112151 appears to describe a patient movement sensor which receives input from at least position sensors and an IR camera. In an embodiment, a fall warning alarm is issued if position sensor data and IR camera data both indicate that a fall has occurred or is about to occur.

US 2012/0314901 describes a fall detection technology in which motion sensor information and image-based analysis is used to detect a fall. In particular, a system may combine motion sensor information with image-based analysis.

SUMMARY OF THE INVENTION

It is an object of the present invention to provide a device, system and method for fall detection with increased accuracy and that enable to optimally manage an emergency situation.

In a first aspect of the present invention a device for fall detection is presented comprising: a sensor input for obtaining sensor data related to movement of a subject acquired by a sensor, a video input for obtaining video data of the subject and/or the subject's environment, an analysis unit for analyzing the obtained sensor data to detect one or more signal features indicative of a potential fall of the subject and for analyzing, if one or more such signal features have been detected, the detected one or more signal features and/or related sensor data in combination with related video data to identify similarities in: changes of the related sensor data and/or the signal features over time; and changes of the video data over time, and an output for issuing a fall detection indication if the level and/or amount of detected similarities exceeds a corresponding threshold.

In a further aspect of the present invention a system for fall detection is presented comprising: a sensor for acquiring sensor data related to movement of a subject, a video acquisition unit for acquiring video data of the subject and/or the subject's environment, and a device as disclosed herein for detecting a potential fall of the subject from the acquired sensor data and video data.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to detect a fall of a subject (i.e. a person) by using a clever combination sensor data related to movement of a subject and video data of the subject and/or the subject's environment. The sensor data is processed to derive signal features the values of which are indicative of a possible fall of the wearer. When a possible fall has been identified, the raw sensor data and/or it derived signal features are processed together with the video data.

An algorithm may e.g. be used to compare the evolution of the received video-based and wearable-based signal/feature streams, looking for similarities in changes of the video-based and wearable-based streams over time. When enough similarities are found, the algorithm may decide that the possible fall is confirmed and may issue an alarm to a user (e.g. a nurse). Further, the video stream from the camera where the correspondence was found may be presented to the user. After assessing the presented picture/video, the user may want to cancel the alarm and/or rush to the location of the selected camera to aid the fallen subject.

Thus, a comparison is made between the way in which sensor data changes with the way in which the video data changes in order to detect a fall. The invention thereby provides a more reliable fall detection device, as the similarity between the progress of a fall, as monitored using two different sensing methods, is used to ascertain whether a fall has occurred or not. This reduces a likelihood that a fall will be falsely detected.

In the event that a number/level of similarities between the video data and sensor data (and/or signal features) exceeds a predetermined threshold (e.g. 10 or more similarities or a correlation score greater than 0.5) then an alert may be issued. A number/level of similarities below this threshold may indicate that a fall was incorrectly detected by the sensor data, and may therefore be a false alarm.

For example, a comparison may be made between a temporal pattern of the sensor data and a temporal pattern of the video data to determine whether there are similarities between the changes of the sensor data and the changes of the video data. A number of maxima and/or minima in a data signal may represent, for example, a pattern of the associated data. In some embodiments a correlation may be performed between the sensor data and the video data.

In embodiments, respective similarities between a plurality of data points of the sensor data over time and a plurality of data points of video data over time are used to determine whether a true fall event has occurred.

In this context, an algorithm may generally use any plurality of distance or similarity measures between the two video data and the sensor data. A similarity measure value may be generated based on the plurality of results (e.g. a correlation coefficient). A (possibly dynamic) threshold may be established for the similarity measure value for triggering the detection. For instance, if a correlation coefficient determined from the video data and the sensor data exceeds the threshold, a similarity between the changes of the video data and the sensor data over time may be assumed to be detected.

Thus, an interdependence between two sets of data (sensor data and image data), each comprising more than one data point, may be determined. This may allow for a more accurate identification of a potential fall by correlating the data. In particular, a correlation between time dependent functions representing the sensor data and the video data respectively may result in a value representative of the similarities between the changes of the sensor data over time and the changes of the video data over time.

Further, video data of the subject's environment may generally be understood as video data of any area and environment where the subject may be encountered, including e.g. the subject's room, the subject's home, but also public areas e.g. around the hospital visible in surveillance cameras.

In an embodiment said analysis unit is configured to identify similarities in timing, speed, duration, intensity and/or evolution of changes. The kind of similarities that are identified may depend on the kind of sensor data and the kind of sensor used for acquiring the sensor data. For instance, signal features and similarities of changes of these signal features may be used that show significant changes and can thus be easily recognized as indicators for a potential fall of the subject.

In an embodiment said analysis unit is configured to detect as signal feature indicative of a potential fall of the subject one or more of impact, maxima, minima, zero crossings, acceleration in vertical direction, velocity in vertical direction, height change, inclination before and/or after a potential fall, activity level before and/or after a potential fall, and intensity change. Such features are particularly helpful and indicative of a potential fall.

Said analysis unit may be configured to detect changes occurring in vertical direction and/or due to impact of the subject on the ground and use such changes in the identification of similarities. Such changes are useful indicators for a potential fall. The detection of changes may relate to changes of position of the subject or of an object. For instance, it may be detected that an object is in one image frame at one position of the image and the same object is detected at another position in a subsequent image frame such that the subsequent position is determined or known to be at a lower position in relation to the local gravitational field.

Said analysis unit may further be configured to estimate the relative vertical velocity and/or acceleration of the subject from the video data and to correlate it with a vertical acceleration and/or vertical velocity derived from the sensor data to identify similarities. This improves the accuracy of the detection of a potential fall.

Said analysis unit may hereby be further configured to determine a vertical velocity map from the video data and estimate the relative vertical velocity and/or acceleration of the subject from said vertical velocity map. The vertical velocity map may thus be used to indicate local velocities, e.g. of different body areas of the subject's body.

Said analysis can also be us to detect a vertical move of an object from a start position to a lower position in another video frame of the video data.

In another embodiment said analysis unit is configured to analyze different video data streams acquired by different video data acquisition units to identify similarities between: changes of the related sensor data and/or the signal features over time; and changes of the video data over time. This ensures a higher accuracy of the detection of a potential fall.

The analysis unit may further be configured to analyze the obtained video data to detect one or more signal features indicative of a potential fall of the subject and to analyze, if in addition to the detection of one or more signal features indicative of a potential fall of the subject indications of a potential fall of the subject have been detected in the video data, the detected one or more signal features and/or the related sensor data in combination with the related video data to identify similarities between: changes of the related sensor data and/or the signal features over time; and changes of the video data over time. The use of the video data already for detecting indications of a potential fall may further improve the detection of a potential fall.

The output is preferably configured to additionally issue a video data portion and/or sensor data portion and/or identified signal features related to an identified potential fall. This may help the user to make an opinion on the situation and to decide on required measures to be taken, e.g. if personal help is immediately required by the subject or if the situation of the subject is harmless. Further, this might help the user to find the location of the fallen subject more easily. In a system using multiple cameras this may include selecting the right camera (e.g. video data from a camera which is linked to a location in the hospital) for presentation to the user (e.g. nurse).

The sensor of the system used for acquiring the sensor data may include one or more sensor elements worn by the subject, e.g. using a sticker, a chest belt, a wristband, etc., or may include one or more sensor elements that are arranged in the subject's environment, e.g. in the bed of the subject. Such sensors may include one or more of a movement sensor, an accelerometer, a pressure sensor, a bed camera and an inertial sensor. Generally any sensor that is able to provide sensor data relating to movement of the subject may be used. For instance, smartphones conventionally include an inertial sensor which may be used as sensor in the proposed system to acquire sensor data related to movement of the subject, as long as the smartphone is carried by the subject, e.g. in the pocket of the subject's jacket or trousers. These sensor elements may provide additional information and/or confirmation that the subject in question is not in the bed but outside of the bed.

The video acquisition unit used for acquiring the video data may include a body-worn camera worn by the subject for acquiring video data of the subject's environment and/or a stationary or mobile camera for acquiring video data of the subject, in particular an RGB camera and/or an infrared camera.

In an embodiment of the system the sensor, the video acquisition unit and the device are integrated into a user device, in particular a smartphone, a camera, a watch or glasses.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
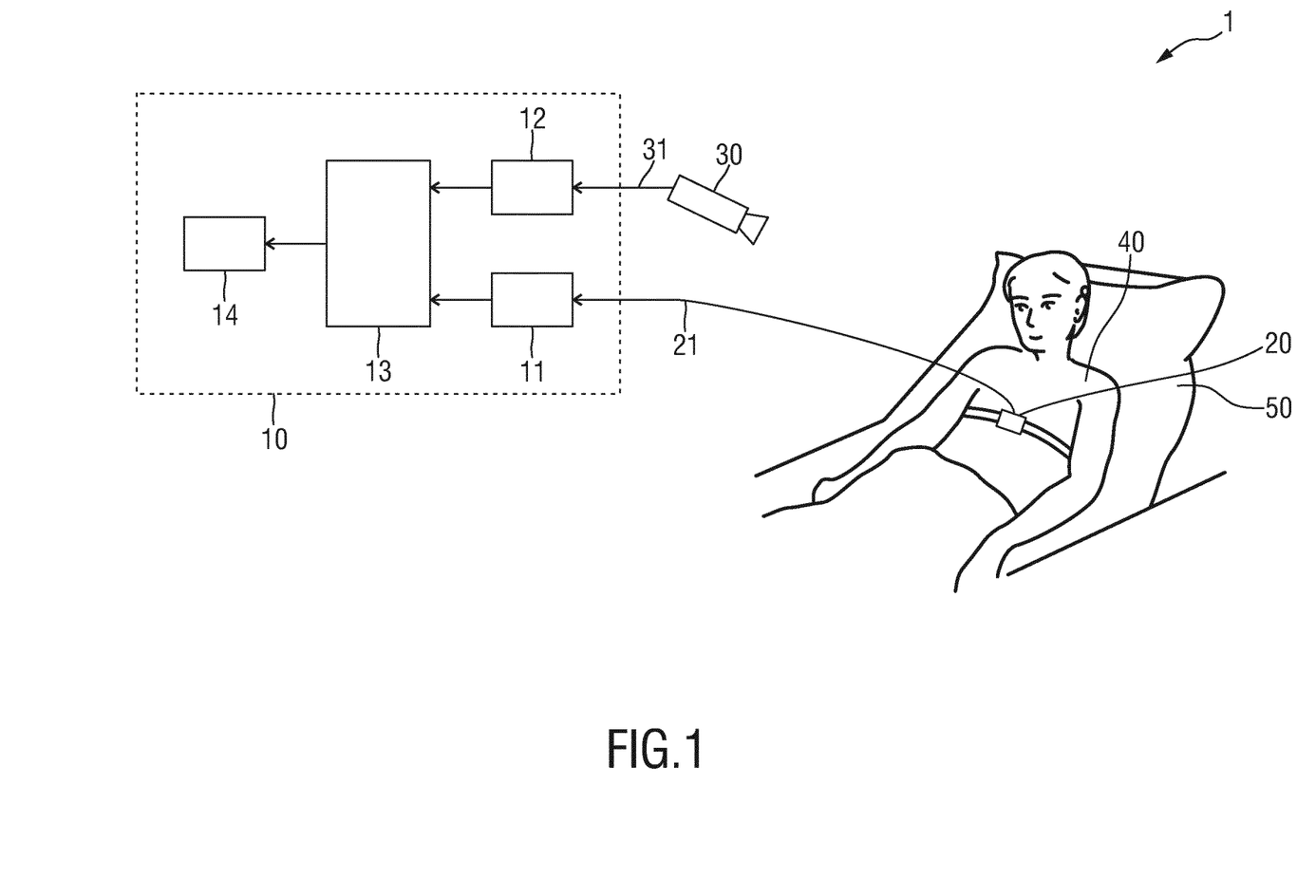
FIG. 1 shows a schematic diagram of a first embodiment of a system and a device according to the present invention.

FIG. 1 shows a schematic diagram of a first embodiment of a system 1 and a device 10 according to the present invention for fall detection of a subject 40, e.g. a patient in a hospital, an elderly person in a care station or rest home, a person at home, a child in a bed, etc. In this example the subject 40 is a patient lying in a bed 50, e.g. in a hospital.

The system 1 comprises at least one sensor 20 for acquiring sensor data related to movement of a subject 40. In this exemplary embodiment the sensor 20 is a body-worn inertial sensor such as an accelerometer that is fixed to the subject's body by a chest belt. The sensor 20 is able to detect movements of the subject's body and to generate sensor data 21 representing such movements.

The system 1 further comprises a video acquisition unit 30 for acquiring video data 31 of the subject and/or the subject's environment, in this case a stationary or mobile camera for acquiring video data of the subject 40, in particular an RGB camera and/or an infrared camera. The camera 30 is e.g. mounted to the ceiling and monitors the whole bed 50 as is commonly the case, for example, in video surveillance applications.

The system 1 further comprises a device 10 for detecting a potential fall of the subject 40 from the acquired sensor data 21 and video data 31. The device 10 comprises a sensor input 11 for obtaining (i.e. receiving or retrieving) the sensor data 21 related to movement of a subject acquired by the sensor 20 and a video input 12 for obtaining (i.e. receiving or retrieving) the video data 31 of the subject 40 and/or the subject's environment (e.g. the bed 50 and the area around the bed 50). For the communication of the sensor data 21 and the video data 31 to the device 10 generally any possible way of communication may be used. For instance, the sensor 20 and the camera 30 may be connected to the device 10 through wires (e.g. directly or via a computer network, such as a LAN) or in a wireless manner, e.g. a communication network (e.g. UMTS, LTE, etc.) or another wireless network (e.g. Wi-Fi, Bluetooth, ZigBee, etc.). The sensor input 11 and the video input 12 may thus e.g. be corresponding data interfaces, such as a Bluetooth interface, a Wi-Fi interface, wired terminals, etc.

The device 10 further comprises an analysis unit 13 for analyzing the obtained sensor data 21 to detect one or more signal features indicative of a potential fall of the subject 40 and for analyzing, if one or more such signal features have been detected, the detected one or more signal features and/or the related sensor data 21 in combination with the related video data 31 to identify similarities of changes of the analyzed signal features, sensor data and video data indicating a potential fall of the subject 40. This operation will be explained in more detail below. The analysis unit 13 may e.g. be implemented in hard- and/or software, as one or more programmed processors or computers (e.g. a hospital workstation, a caregiver's PC, etc.) or as an application running on a user device (e.g. a smartphone, laptop, tablet, etc.).

The device 10 further comprises an output 14 for issuing a fall detection indication if the level and/or amount of detected similarities exceeds a corresponding threshold. The output 14 may e.g. an output interface for communicating the fall detection indication, e.g. an alarm notice, to a remote destination, e.g. a nurse's user device, a central supervision monitor, etc., or may be a user interface, like a display and/or loudspeaker, that directly issues a (visible and/or audible) notice that a potential fall of a particular subject has been detected.

Thus, according to the present invention, potential user falls are detected by using a combination of sensor data and video (camera) data.

Figure 2:
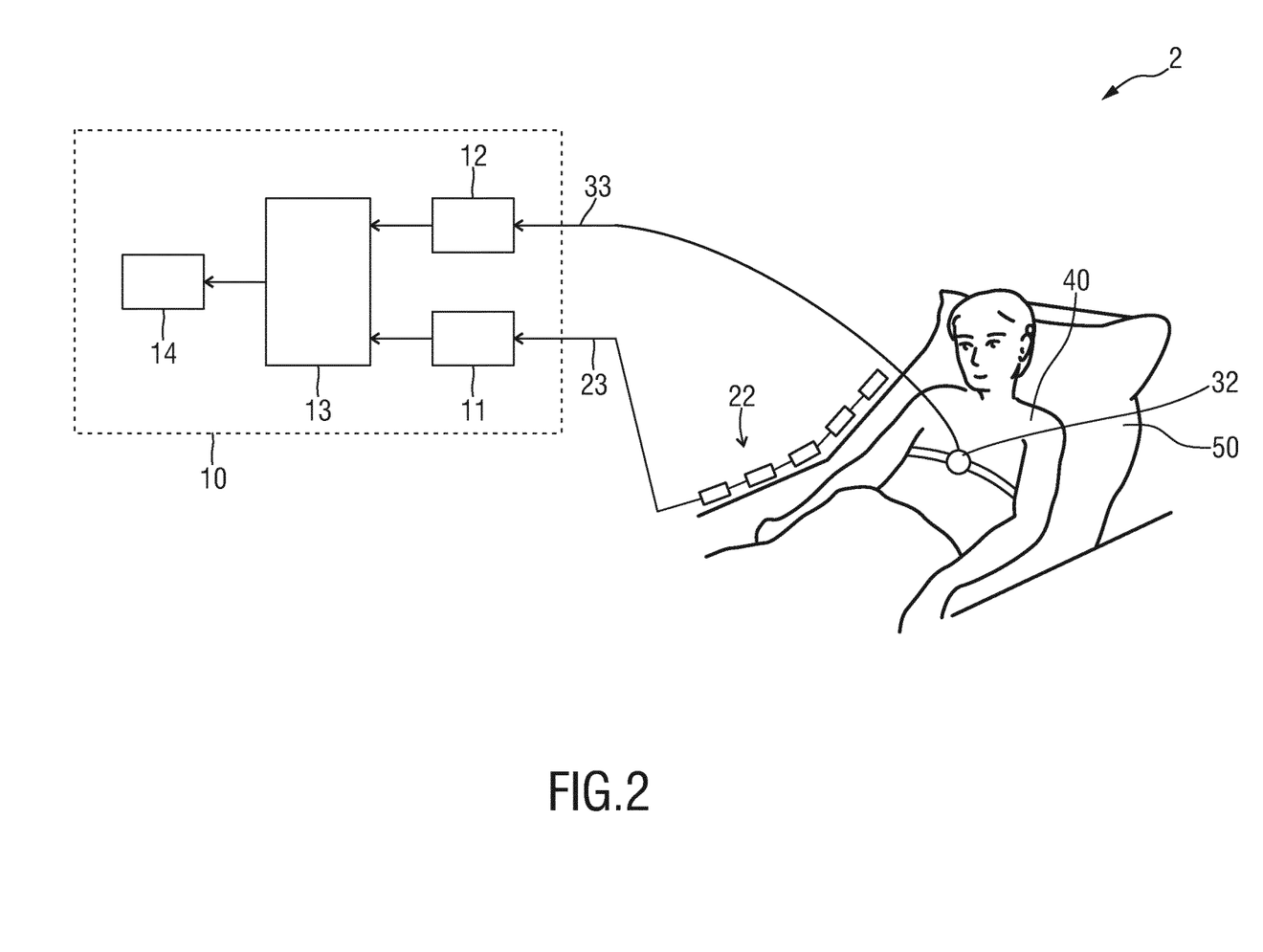
FIG. 2 shows a schematic diagram of a second embodiment of a system and a device according to the present invention.

FIG. 2 shows a schematic diagram of a second embodiment of a system 2 and a device 10 according to the present invention. The device 10 in this embodiment generally has the same layout as the device 10 shown in FIG. 1. Instead of (or in addition to) the body-worn sensor 20 one or more pressure sensors 22 (e.g. an array of pressure sensors) are used that are in this exemplary embodiment arranged within or on top of the mattress and acquire sensor data 23 that reflect movements of the subject 40. Further, instead of (or in addition to) the stationary camera 30 a body-worn camera 32 is worn by the subject 40 for acquiring video data 33 of the subject's environment. Like in the first embodiment the device 10 obtains the sensor data 23 and the video data 33 and processes them to detect a potential fall of the subject.

The use of a body worn camera 32 has the advantage that the subject 40 can walk around and that also falls of the subject during walking, e.g. in the bathroom, on the stairs, etc., can be detected, provided the subject 40 wears a body-worn sensor 20 as shown in the first embodiment. Alternatively or in addition, a larger area, e.g. a complete home or hospital station may be provided with a plurality of cameras that monitor a larger area, i.e. the analysis unit 13 obtains and analyses video data from a plurality of cameras.

Figure 3:
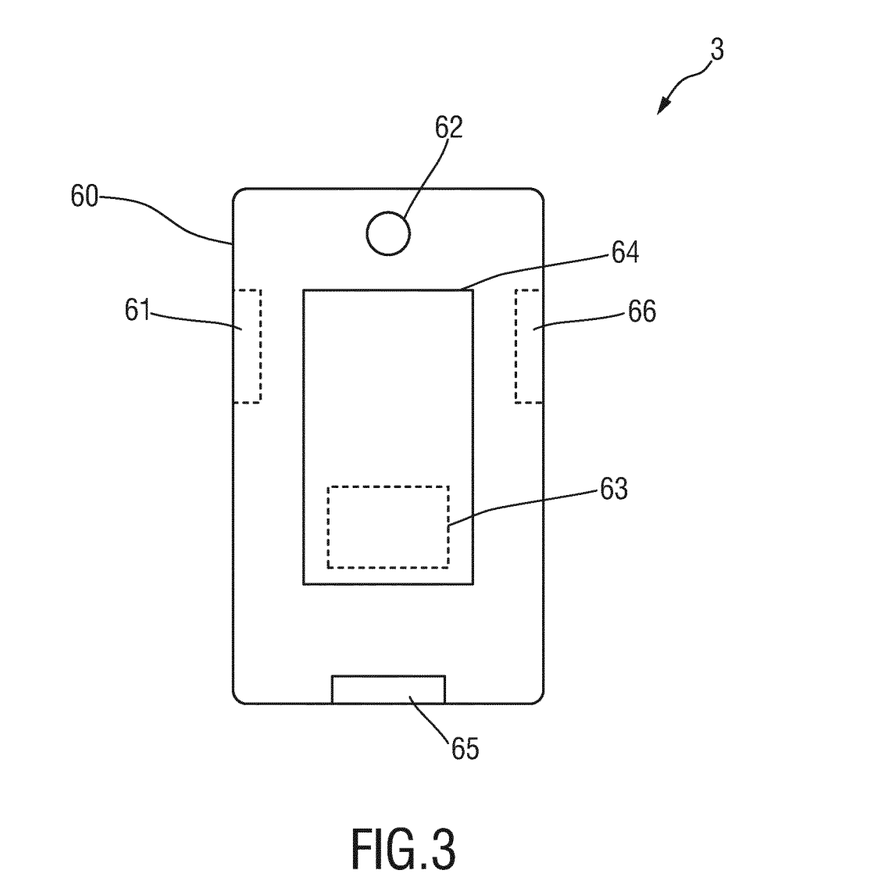
FIG. 3 shows a schematic diagram of a third embodiment of a system and a device according to the present invention.

FIG. 3 shows a schematic diagram of a third embodiment of a system 3 and a device 10 according to the present invention. In this embodiment all elements of the system 3 are integrated into a user device 60, in this exemplary embodiment into a smartphone. The system 3 thus makes use of the smartphone's inertial sensor 61 (as sensor for acquiring sensor data related to movement of a subject wearing the smartphone), the smartphone's camera 62 (as video acquisition unit for acquiring video data of the subject's environment), the smartphone's processor 63 (as analysis unit) and the smartphone's display 64, loudspeaker 65 and/or communication means 66 (e.g. Wi-Fi interface, radio antenna, etc.) (as output unit). In other embodiments, the elements of the system may be integrated in other user devices such as a watch, camera, glasses (e.g. Google glass), etc.

The user device, in this exemplary embodiment the smartphone, may be worn as a pendant or attached to the clothes. In this case, upon positive fall detection, the video stream is sent to the user, e.g. a nurse, who can determine the severity of the fall from the video data (e.g. whether the subject is lying on the floor after the event). The location of the fall may also be determined based on the video data.

According to an embodiment of the present invention the sensor data is processed to derive signal features the values of which are indicative of a possible fall of the subject. Such signal features may be one or more of impact, maxima/minima/zero-crossings of the accelerometer norm (e.g. of 3-axis acceleration vector data), vertical acceleration, vertical velocity, inclination before/after the event, activity level before/after the event, and height change estimates. When a possible fall has been identified, the raw sensor data and/or its derived signal features are transmitted to the analysis unit, which has also access to the video data stream of one or more video cameras.

An algorithm may then be used to compare the evolution of the received video-based and sensor-based signal/feature streams, looking for similarities such as in timing, speed and evolution of changes. Changes that occur in the vertical axis (e.g. during a person's descent to the ground) and/or due to the impact on the ground are of special relevance. In one embodiment an image area corresponding to the subject is segmented and tracked from one frame (of the video data) to another. The relative vertical velocity of the $k^{th}$ object $v_z(k,t)$ as a function of time t is estimated in segments of a few frames. In another embodiment the vertical motion velocity in the image plane is estimated for all points to obtain a vertical velocity map $v_z(i, j, t)$ where i and j are positions in the image plane. In the first case a vertical velocity corresponding to a number of objects in the image may be obtained. In the second case the velocity may be computed for a number of areas in the image. There are conversions between the two representations of vertical motion in the image.

In the following the case based on single object tracking will be described in more detail, but the extension to the cases of multiple objects and full motion flow image can be handled similarly.

The vertical velocity of a single object (such as a person's body) in the plane is $v_z(t)$. The observed vertical acceleration from the accelerometer signal is given by $a_z(t)$. In order to determine the temporal correlation between the two signals it is first necessary to bring them to the same representation domain. In a preferred embodiment the correlation coefficient between the first time derivative of the object velocity and the vertical acceleration is estimated, i.e.

$$c_a = C\left(\frac{dv_z(t)}{dt}, a_z(t)\right). \quad (1)$$

In another embodiment a cumulative integral of the vertical acceleration (from the accelerometer signal) is taken to obtain an estimate for the vertical velocity, i.e.

$$\dot{a}_z(t) = \int_0^t a\_z(t)dt \quad (2)$$

and the correlation is then computed from $$c_v = C(v_z(t), \dot{a}_z(t)). \quad (3)$$

The step-size between the time points (i.e. the size of a discretized dt) when performing the calculation of equations (1) and (2) is less than the event length of a potential fall. For example, the step-size may be less than 0.1 s or less than 0.1 ms.

A plurality of data points for each of the sensor data and video data are taken over time. Thus, multiple data points are used for performing a similarity check. The correlation computation calculates the relationship between these data points, to give a measure of the similarities (i.e. a similarity measure value) between the between changes of the sensor data over time and changes of the video data over time.

In this way, a comparison is made between changes in the sensor data over time (here: changes of acceleration) and changes in the video data (here: change in velocity) over time. A correlation is computed to provide a measure of the similarities between the changes in the sensor data and changes in the video data.

A value of this correlation may be compared to a threshold value to determine whether or not a fall has occurred. By way of example, a correlation value greater than 0.5 or 0.6 may indicate that a fall is likely to have occurred.

Thus, the video-based and sensor-based signal/feature streams are compared, using a plurality of data points of said streams, to determine whether or not a fall has occurred.

The features to correlate the sensor data (in particular accelerometer data) with the video data can also be unrelated to those exclusively calculated for a fall detection algorithm, e.g. a step detection gait feature that is already computed on the sensor, with the advantage that there is no additional effort needed for feature computation.

There are several alternative options for comparing the video-based and sensor-based signal/feature streams, which will be described below. The correlation operation typically contains normalization (e.g. using Pearson correlation coefficient) such that correlation values between the sensor data and the video data can be compared at different times. In addition, the normalization may contain removal of the mean value in the observation frame and other pre-processing steps. In a typical case, the correlation is computed between several objects or image regions in images from multiple cameras.

When enough similarity is found between the video-based and sensor-based signal/feature streams, it is decided (e.g. by the algorithm) that the possible fall is confirmed and an alarm may e.g. be issued to a user (e.g. a nurse), preferably while presenting the video stream from the camera where the correspondence was found.

The automatic selection and presentation of the relevant camera and the relevant camera stream prevents an excess of information to the user and provides information on the location of the subject. The presented video stream is preferably real time, but also can show recording around the fall event (e.g. few seconds before and after the event) to assess the severity of the fall. Moreover, if multiple cameras have reached the required level of similarity with the sensor signal, then multiple video streams could be presented, either alternatively in one frame or simultaneously in different sub-frames. The presentation of the fall alarm and of the video stream(s) may take place in a user device, such as a user's PC, laptop, smartphone, tablet, smart watch, etc.

Optionally, the video data may, in addition to the sensor data, be used in the first step of the analysis to detect one or more signal features indicative of a potential fall of the subject.

Although the use of stationary cameras is preferred, mobile cameras may also be utilized (e.g. nursing robot with camera patrolling the hospital ward). In that case, the mobile cameras should incorporate a means of communicating their location to the system so that the fallen subject can be optimally found by the user.

Optionally, passive infrared (PIR) cameras may be also included in the system. Such cameras should be capable of outputting a pixelated image stream that is susceptible of being processed by the algorithms described herewith. The additional advantage introduced by PIR cameras would be a privacy improvement. They would therefore be especially suitable for extending system coverage to sensitive areas like toilets and bathrooms, in which people may too suffer from a fall.

In an embodiment, part of the analysis may also run on the sensor. For instance, the analysis to detect one or more signal features indicative of a potential fall of the subject based on the sensor data may run locally on the sensor, which may thus be equipped with a corresponding processing capability, e.g. a small processor. In that case, when a possible fall is detected the sensor may temporarily adapt its radio transmission settings for facilitating the correct and timely reception of the pre-alarm, signal/feature stream or other relevant information at the backend. The adaptation of the radio settings may include one or more of higher transmit power, transmission over all available channels/RF interfaces, switching to acknowledged-transmission mode, and relaying alarms between sensors and other elements of the system.

The present invention may be implemented as an app (application program) for a smartphone (or smart watch or Google glass) that is worn by subject, e.g. unobtrusively in their pocket or bag. When e.g. the smartphone is connected to the hospital network, the signal features will be automatically calculated and transmitted.

The present invention can be used in application settings in which assistance or care are required in relation to falls of subjects. It is therefore applicable to in-patient care settings such a hospital wards as well as patient/customer care settings such as (elderly) residential care and home care. It is generally applicable to all situations where a fall of a subject shall be detected, e.g. a fall of a baby out of the bed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for fall detection, said device comprising:
a sensor input for obtaining sensor data related to movement of a subject acquired by a sensor,
a video input for obtaining video data of the subject and/or the subject's environment,
an analysis unit configured to estimate a relative vertical velocity and/or acceleration of the subject from the video data and to correlate it with a vertical acceleration and/or vertical velocity derived from the sensor data to identify similarities:
for analyzing the obtained sensor data to detect one or more signal features indicative of a potential fall of the subject and
for analyzing, if one or more such signal features have been detected, the detected one or more signal features and/or related sensor data in combination with related video data to identify similarities between: changes of the related sensor data and/or the signal features over time; and changes of the video data over time;
the analysis unit configured to determine a vertical velocity map from the video data and estimate the relative vertical velocity and/or acceleration of the subject from said vertical velocity map; and
an output for issuing a fall detection indication if the level and/or amount of detected similarities exceeds a corresponding threshold.

2. The device as claimed in claim 1,
wherein said analysis unit is configured to identify similarities in changes of timing, speed, duration, and/or intensity.

3. The device as claimed in claim 1,
wherein said analysis unit is configured to detect as signal feature indicative of a potential fall of the subject one or more of impact, maxima, minima, zero crossings, acceleration in vertical direction, velocity in vertical direction, height change, inclination before and/or after a potential fall, activity level before and/or after a potential fall, and intensity change.

4. The device as claimed in claim 1,
wherein said analysis unit is configured to detect changes occurring over time in vertical direction and/or due to impact of the subject on the ground and use such changes in the identification of similarities.

5. The device as claimed in claim 1,
wherein said analysis unit is configured to analyze different video data streams acquired by different video data acquisition units to identify similarities of changes with the analyzed signal features and/or sensor data.

6. The device as claimed in claim 1,
wherein said analysis unit is configured to analyze the obtained video data to detect one or more signal features indicative of a potential fall of the subject and to analyze, if in addition to the detection of one or more signal features indicative of a potential fall of the subject indications of a potential fall of the subject have been detected in the video data, the detected one or more signal features and/or the related sensor data in combination with the related video data to identify similarities of changes of the analyzed signal features, sensor data and video data indicating a potential fall of the subject.

7. The device as claimed in claim 1,
wherein said output is configured to additionally issue a video data portion and/or sensor data portion and/or identified signal features related to an identified potential fall.

8. A system for fall detection, said system comprising:
a sensor for acquiring sensor data related to movement of a subject,
a video acquisition unit for acquiring video data of the subject and/or the subject's environment, and
a device as claimed in claim 1 for detecting a potential fall of the subject from the acquired sensor data and video data.

9. The system as claimed in claim 8,
wherein said sensor includes one or more of a movement sensor, an accelerometer, a pressure sensor and an inertial sensor.

10. The system as claimed in claim 8,
wherein said video acquisition unit includes a body-worn camera worn by the subject for acquiring video data of the subject's environment and/or a stationary or mobile camera for acquiring video data of the subject, in particular an RGB camera and/or an infrared camera.

11. The system as claimed in claim 8,
wherein the sensor, the video acquisition unit and the device are integrated into a user device, in particular a smartphone, a camera, a watch or glasses.

12. A non-transitory computer program comprising program code means for causing a computer to carry out the steps of a method for fall detection, said method comprising:
obtaining sensor data related to movement of a subject acquired by a sensor,
obtaining video data of the subject and/or the subject's environment,
analyzing the obtained sensor data to detect one or more signal features indicative of a potential fall of the subject,
analyzing, if one or more such signal features have been detected, the detected one or more signal features and/or related sensor data in combination with related video data to identify similarities between: changes of the related sensor data and/or the signal features over time; and changes of the video data over time,
estimating a relative vertical velocity and/or acceleration of the subject from the video data and correlating it with a vertical acceleration and/or vertical velocity derived from the sensor data to identify similarities to determine a vertical velocity map from the video data,
estimating the relative vertical velocity and/or acceleration of the subject from said vertical velocity map; and
issuing a fall detection indication if the level and/or amount of detected similarities exceeds a corresponding threshold.

13. The device as claimed in claim 1,
wherein said analysis unit is configured to analyze the detected one or more signal features and/or relative sensor data in combination with the related video data in response to the signal features indicating that a possible fall has been identified.

* * * * *